(12) United States Patent
Matsumura et al.

(10) Patent No.: US 9,173,945 B2
(45) Date of Patent: Nov. 3, 2015

(54) OPHTHALMOLOGICAL AQUEOUS COMPOSITION

(71) Applicant: ROHTO PHARMACEUTICAL CO., LTD., Osaka-shi, Osaka (JP)

(72) Inventors: Yasuko Matsumura, Osaka (JP); Chinatsu Furumiya, Osaka (JP); Masashi Itoh, Osaka (JP)

(73) Assignee: ROHTO PHARMACEUTICAL CO., LTD., Osaka-Shi (JP)

( * ) Notice: Subject to any disclaimer, the term of this patent is extended or adjusted under 35 U.S.C. 154(b) by 0 days.

(21) Appl. No.: 14/355,350

(22) PCT Filed: Oct. 31, 2012

(86) PCT No.: PCT/JP2012/078128
§ 371 (c)(1),
(2) Date: Apr. 30, 2014

(87) PCT Pub. No.: WO2013/065720
PCT Pub. Date: May 10, 2013

(65) Prior Publication Data
US 2014/0308368 A1    Oct. 16, 2014

(30) Foreign Application Priority Data
Nov. 1, 2011   (JP) .................................. 2011-240167

(51) Int. Cl.
| | | |
|---|---|---|
| *A61F 2/00* | (2006.01) | |
| *A61K 47/38* | (2006.01) | |
| *A61K 9/08* | (2006.01) | |
| *A61K 31/045* | (2006.01) | |
| *A61K 31/122* | (2006.01) | |
| *A61K 31/125* | (2006.01) | |
| *A61K 33/30* | (2006.01) | |
| *A61K 9/00* | (2006.01) | |
| *A61K 47/10* | (2006.01) | |
| *A61K 47/32* | (2006.01) | |
| *A61K 47/36* | (2006.01) | |

(52) U.S. Cl.
CPC ............... *A61K 47/38* (2013.01); *A61K 9/0048* (2013.01); *A61K 9/08* (2013.01); *A61K 31/045* (2013.01); *A61K 31/122* (2013.01); *A61K 31/125* (2013.01); *A61K 33/30* (2013.01); *A61K 47/10* (2013.01); *A61K 47/32* (2013.01); *A61K 47/36* (2013.01)

(58) Field of Classification Search
None
See application file for complete search history.

(56) References Cited

U.S. PATENT DOCUMENTS

| 5,688,532 | A  | * | 11/1997 | Bryce-Smith ................. 424/641 |
|---|---|---|---|---|
| 2005/0137166 | A1 | * | 6/2005 | Asgharian et al. ............. 514/54 |
| 2006/0047006 | A1 | | 3/2006 | Salamone et al. |
| 2009/0176737 | A1 | | 7/2009 | Tabuchi et al. |
| 2010/0021562 | A1 | | 1/2010 | Chowhan et al. |
| 2010/0137252 | A1 | * | 6/2010 | Matsumura et al. ........... 514/78 |
| 2010/0239518 | A1 | | 9/2010 | Matsumura et al. |
| 2012/0269760 | A1 | | 10/2012 | Akagi et al. |

FOREIGN PATENT DOCUMENTS

| JP | 2002-3364 A | 1/2002 |
|---|---|---|
| JP | 2003-146892 A | 5/2003 |
| JP | 2005-162747 A | 6/2005 |
| JP | 2006-22087 A | 1/2006 |
| JP | 2006-249076 A | 9/2006 |
| JP | 2008-510568 A | 4/2008 |
| JP | 2008-189677 A | 8/2008 |
| JP | 2009-46480 A | 3/2009 |
| JP | 2010-504990 A | 2/2010 |
| JP | 2011-93888 A | 5/2011 |
| WO | 2007/077783 A1 | 7/2007 |
| WO | 2009/035034 A1 | 3/2009 |

* cited by examiner

*Primary Examiner* — Susan Tran
(74) *Attorney, Agent, or Firm* — Birch, Stewart, Kolasch & Birch, LLP (57) ABSTRACT

The present invention provides an aqueous ophthalmic composition containing (A) a terpenoid, (B) zinc chloride, and (C) at least one member selected from the group consisting of cellulose-based polymeric compounds, vinyl-based polymeric compounds, polyethylene glycols and dextran. According to the present invention, an aqueous ophthalmic composition is provided in which adsorption of the terpenoid to a container can be inhibited, thereby making it possible to inhibit the reduction in the terpenoid content for a long period of time, the aqueous ophthalmic composition having some excellent actions such as an inhibitory action for histamine release, and an inhibitory action for discharges from the eyes.

3 Claims, 1 Drawing Sheet

OPHTHALMOLOGICAL AQUEOUS COMPOSITION

TECHNICAL FIELD

The present invention relates to an aqueous ophthalmic composition. More particularly, the present invention relates to an aqueous ophthalmic solution in which adsorption of a terpenoid to a container is inhibited, and a method for inhibiting adsorption of a terpenoid to a container in an aqueous ophthalmic composition.

BACKGROUND ART

In ophthalmic compositions, a terpenoid such as menthol is contained in order to give a refreshing feel. However, when an ophthalmic composition containing a terpenoid is filled in a plastic container or the like, the terpenoid adsorbs to the container during storage, so that the content of the terpenoid is reduced. The reduction in the content of the terpenoid has some disadvantages of impairing feel of use because the reduction greatly influences the senses of the ophthalmic compositions, and further impairing qualities of the ophthalmic compositions. On the other hand, a method of inhibiting adsorption of a terpenoid to a plastic container by adding a surfactant (Patent Publications 1 and 2). However, surfactants may irritate ocular mucous membranes, so that it is said that some side effects are caused, such as disorders are caused in the cornea if, for example, eye drops containing surfactants are frequently dropped or if individuals having disorders in the cornea or individuals whose teard flow is are not normal showing dry eye symptoms and the like are dropped, so that there are some concerns in the aspect of safety.

On the other hand, a zinc salt such as zinc sulfate or zinc lactate has constrictive actions and anti-inflammatory actions, and has been used widely in eye drops as constrictive agents and anti-inflammatory agents, and zinc chloride or zinc sulfate has also been known as a bactericidal agent. However, the influences which these components would have on the aqueous ophthalmic compositions containing terpenoids have not been elucidated.

PRIOR ART REFERENCES

Patent Publications

Patent Publication 1: Japanese Patent Laid-Open No. 2002-003364
Patent Publication 2: Japanese Patent Laid-Open No. 2005-162747

SUMMARY OF THE INVENTION

Problems to be Solved by the Invention

The present invention has been accomplished in view of the current situations of the prior art mentioned above, and an object thereof is to provide an aqueous ophthalmic composition containing a terpenoid, the aqueous ophthalmic composition capable of inhibiting the adsorption of terpenoids to the container, thereby maintaining a high residual ratio of terpenoids in the aqueous ophthalmic composition, and further to provide a method for inhibiting the adsorption of the terpenoids contained in the aqueous ophthalmic composition.

Furthermore, another object of the present invention is to provide an aqueous ophthalmic composition having other more improved actions.

Means to Solve the Problems

The present inventor has made intensive studies in order to accomplish the objects mentioned above. As a result, it has been found that in the aqueous ophthalmic composition containing a terpenoid, at least one member selected from the group consisting of cellulose-based polymeric compounds, vinyl-based polymeric compounds, polyethylene glycols and dextran is combined together with zinc chloride, whereby the adsorption of the terpenoid to the container can be inhibited when the aqueous ophthalmic composition is filled in various containers such as plastic containers and stored, thereby making it possible to inhibit the reduction in the terpenoid content for a long period of time. In addition, the present inventor has found that the aqueous ophthalmic composition containing the above ingredients markedly has an inhibitory action for histamine release, and further has an unexpected action of effectively inhibiting discharges from the eyes. The present invention has been perfected as a result of further studies based on these findings.

In other words, the present invention provides an aqueous ophthalmic composition of the embodiments listed hereinbelow.

Item 1-1: An aqueous ophthalmic composition containing (A) a terpenoid, (B) zinc chloride, and (C) at least one member selected from the group consisting of cellulose-based polymeric compounds, vinyl-based polymeric compounds, polyethylene glycols and dextran.

Item 1-2: The aqueous ophthalmic composition according to the above item 1-1, wherein the terpenoid is at least one member selected from the group consisting of menthol, menthone, camphor, borneol, and geraniol.

Item 1-3. The aqueous ophthalmic composition according to the above item 1-1 or 1-2, wherein the content proportion of the terpenoid in total is from 0.00001 to 0.2 w/v %, on the basis of a total amount of the aqueous ophthalmic composition.

Item 1-4: The aqueous ophthalmic composition according to any one of the above items 1-1 to 1-3, wherein the zinc chloride is contained in an amount of from 0.000005 to 5,000 parts by weight, based on 1 part by weight of a total amount of the terpenoids.

Item 1-5: The aqueous ophthalmic composition according to any one of the above items 1-1 to 1-4, wherein the component (C) is contained in an amount of from 0.0005 to 1,000,000 parts by weight in total, based on 1 part by weight of a total amount of the terpenoids.

Item 1-6: The aqueous ophthalmic composition according to any one of the above items 1-1 to 1-5, wherein the component (C) is at least one member selected from the group consisting of hydroxyethyl cellulose, hydroxypropylmethyl cellulose, carboxymethyl cellulose, carboxymethyl cellulose sodium, polyvinyl pyrrolidone, dextran, and polyethylene glycol.

Item 1-7: The aqueous ophthalmic composition according to any one of the above items 1-1 to 1-6, further comprising a surfactant.

Item 1-8: The aqueous ophthalmic composition according to any one of the above items 1-1 to 1-7, wherein the composition is housed in a container made of a material containing at least one plastic selected from the group consisting of polyethylene terephthalate resins, polypropylene resins, polyethylene resins, and polyethylene naphthalate resins.

Also, the present invention provides a method for inhibiting adsorption of a terpenoid to a container in the aqueous ophthalmic composition, or a method for inhibiting the reduction in the content of a terpenoid, of the embodiments listed hereinbelow.

Item 2-1: A method for inhibiting adsorption of a terpenoid to a container in an aqueous ophthalmic composition, including combining in the aqueous ophthalmic composition (B) zinc chloride and (C) at least one member selected from the group consisting of cellulose-based polymeric compounds, vinyl-based polymeric compounds, polyethylene glycols and dextran, together with (A) a terpenoid.

Item 2-2: A method for inhibiting the reduction in the content of a terpenoid in an aqueous ophthalmic composition, including combining in the aqueous ophthalmic composition (B) zinc chloride and (C) at least one member selected from the group consisting of cellulose-based polymeric compounds, vinyl-based polymeric compounds, polyethylene glycols and dextran, together with (A) a terpenoid.

Further, the present invention also provides a method for enhancing an inhibitory action for histamine release of the aqueous ophthalmic composition, or a method for giving an inhibitory action for discharges from the eyes to the aqueous ophthalmic composition, of the embodiments listed hereinbelow.

Item 3-1. A method for enhancing an inhibitory action for histamine release of an aqueous ophthalmic composition, including combining in the aqueous ophthalmic composition (A) a terpenoid, (B) zinc chloride, and (C) at least one member selected from the group consisting of cellulose-based polymeric compounds, vinyl-based polymeric compounds, polyethylene glycols and dextran.

Item 3-2. A method for giving an inhibitory action for discharges from the eyes to the aqueous ophthalmic composition, including combining in the aqueous ophthalmic composition (A) a terpenoid, (B) zinc chloride, and (C) at least one member selected from the group consisting of cellulose-based polymeric compounds, vinyl-based polymeric compounds, polyethylene glycols and dextran.

Further, the present invention also provides a method for inhibiting or treating itchiness of the eyes, or a method for inhibiting discharges from the eyes, of the embodiments listed hereinbelow.

Item 4-1. A method for inhibiting or treating itchiness of the eyes, including contacting an aqueous ophthalmic composition containing (A) a terpenoid, (B) zinc chloride, and (C) at least one member selected from the group consisting of cellulose-based polymeric compounds, vinyl-based polymeric compounds, polyethylene glycols and dextran with cornea and/or conjunctiva.

Item 4-2. A method for inhibiting discharges from the eyes, including contacting an aqueous ophthalmic composition containing (A) a terpenoid, (B) zinc chloride, and (C) at least one member selected from the group consisting of cellulose-based polymeric compounds, vinyl-based polymeric compounds, polyethylene glycols and dextran with cornea and/or conjunctiva.

Further, the present invention also provides use of the embodiments listed hereinbelow.

Item 5. Use of (A) a terpenoid, (B) zinc chloride, and (C) at least one member selected from the group consisting of cellulose-based polymeric compounds, vinyl-based polymeric compounds, polyethylene glycols and dextran, in the manufacture of an aqueous ophthalmic composition having an action for inhibiting adsorption to a container of a terpenoid, an enhanced inhibitory action for histamine release, or an inhibitory action for discharges from the eyes.

Further, the present invention also provides use of the embodiments listed hereinbelow.

Item 6-1. Use of a composition containing (A) a terpenoid, (B) zinc chloride, and (C) at least one member selected from the group consisting of cellulose-based polymeric compounds, vinyl-based polymeric compounds, polyethylene glycols and dextran, as an aqueous ophthalmic composition having an action for inhibiting adsorption to a container of a terpenoid, an enhanced inhibitory action for histamine release, or an inhibitory action for discharges from the eyes.

Item 6-2. Use according to the above item 6-1, wherein the composition is a composition as defined in any one of the above items 1-2 to 1-8.

Further, the present invention also provides a composition of the embodiments listed hereinbelow.

Item 7-1. A composition containing (A) a terpenoid, (B) zinc chloride, and (C) at least one member selected from the group consisting of cellulose-based polymeric compounds, vinyl-based polymeric compounds, polyethylene glycols and dextran, for use in an aqueous ophthalmic composition having an action for inhibiting adsorption to a container of a terpenoid, an enhanced inhibitory action for histamine release, or an inhibitory action for discharges from the eyes.

Item 7-2. The composition according to the above item 7-1, wherein the composition is a composition as defined in any one of the above items 1-2 to 1-8.

Further, the present invention also provides a method for producing an aqueous ophthalmic composition of the embodiments listed hereinbelow.

Item 8-1. A method for producing an aqueous ophthalmic composition having an action for inhibiting adsorption to a container of a terpenoid, an enhanced inhibitory action for histamine release, or an inhibitory action for discharges from the eyes, including adding (A) a terpenoid, (B) zinc chloride, and (C) at least one member selected from the group consisting of cellulose-based polymeric compounds, vinyl-based polymeric compounds, polyethylene glycols and dextran, to a carrier containing water.

Item 8-2. The method according to the above item 8-1, wherein the composition is a composition as defined in any one of the above items 1-2 to 1-8.

Effects of the Invention

According to the aqueous ophthalmic composition of the present invention, in an aqueous ophthalmic composition containing a terpenoid, the adsorption of the terpenoid to the container is inhibited, so that the reduction in the content of the terpenoid can be inhibited in the aqueous ophthalmic composition over a long period of time even during, for example, distribution process and the like. Since the reduction in the terpenoid content in the aqueous ophthalmic composition greatly affects feel of use, the compliance of patients can also be improved by inhibiting the reduction in the terpenoid content.

Further, the aqueous ophthalmic composition of the present invention has an excellent action of inhibiting histamine release. Accordingly, the composition of the present invention is used as an eye drop or an eyewash to contact the composition with cornea by a method such as dropping or eye-washing, thereby anti-histamine action is enhanced, so that the itchiness of the eyes can be inhibited or treated. Therefore, the aqueous ophthalmic composition of the present invention is useful as an eye drop or eyewash for inhibiting itchiness, and the composition is further useful as eye drops or the like for allergies, for inflammation, or for dry eyes, for wearing or putting on contact lens that accompany itchy symptoms.

In addition, the aqueous ophthalmic composition of the present invention has an action of effectively inhibiting discharges from the eyes. Accordingly, the composition of the present invention is contacted with cornea by a method such as dropping or eye-washing, whereby the amount of discharges from the eyes can be inhibited against patients showing symptoms of discharges from the eyes, so that, for example, ease in opening eyes, ease in blinking, blurriness of eyes, or the like can be ameliorated.

MODES FOR CARRYING OUT THE INVENTION

1. Aqueous Ophthalmic Composition

The aqueous ophthalmic composition of the present invention is an aqueous composition containing (A) a terpenoid, (B) zinc chloride, and (C) at least one member selected from the group consisting of cellulose-based polymeric compounds, vinyl-based polymeric compounds, polyethylene glycols and dextran.

The term "aqueous composition" as used herein is a composition containing water. The content proportion of water in the aqueous ophthalmic composition of the present invention is, for example, from 10 to 99.8 w/v %, preferably from 55 to 99.0 w/v %, more preferably from 70 to 98.0 w/v %, even more preferably from 85 to 98.0 w/v %, and especially preferably from 90 to 98.0 w/v %, on the basis of a total amount of the aqueous ophthalmic composition.

The aqueous ophthalmic composition of the present invention will be explained concretely hereinbelow.

(1) Terpenoid

The terpenoid (hereinafter also expressed as the component (A)) is a known compound having a structure having an isoprene unit as a constituting unit, which has been used as a cooling agent.

In the aqueous ophthalmic composition of the present invention, the terpenoid can be used without particular limitations so long as the terpenoid is pharmacologically (pharmaceutically) or physiologically acceptable in the field of medicine. The terpenoid as described above concretely includes menthol, menthone, camphor, borneol, geraniol, cineol, citronellol, carvone, anethole, eugenol, limonene, linalool, linalyl acetate, derivatives thereof, and the like. These compounds may be in any of d-form, 1-form, and dl-form.

In addition, in the present invention, an essential oil containing the above compound may be used as a terpenoid. The essential oil as mentioned above includes, for example, eucalyptus oil, bergamot oil, peppermint oil, cool-mint oil, spearmint oil, Japanese mint oil, fennel oil, cinnamon oil, rose oil, camphor oil, and the like.

The terpenoids may be used alone, or two or more kinds may be optionally combined and used.

Among these terpenoids, menthol, menthone, camphor, borneol, geraniol, and the like are preferred, menthol and camphor are more preferred, 1-menthol, dl-menthol, d-camphor, and dl-camphor are even more preferred, and 1-menthol is especially preferred.

The content proportion of the terpenoid in the aqueous ophthalmic composition of the present invention can be appropriately set depending upon the concrete kinds of the ophthalmic composition. As one example, the content proportion of the component (A) is in total from 0.00001 to 0.5 w/v %, preferably from 0.0005 to 0.25 w/v %, and more preferably from 0.001 to 0.1 w/v %, on the basis of a total amount of the aqueous ophthalmic composition. In addition, it is needless to say that the content proportion can be increased or decreased, by the number of administration, the method of administration, or the like.

(2) Zinc Chloride

In the aqueous ophthalmic composition of the present invention, zinc chloride (hereinafter also expressed as the component (B)) can be used without particular limitations, so long as zinc chloride can be used in the aqueous ophthalmic composition. For example, zinc chloride as prescribed in The Japanese Pharmacopeia Sixteenth Edition can be used.

The content proportion of the zinc chloride in the aqueous ophthalmic composition of the present invention is not particularly limited. As one example, the content proportion of the zinc chloride is from 0.000001 to 0.05 w/v %, preferably from 0.00005 to 0.025 w/v %, and more preferably from 0.0001 to 0.015 w/v %, on the basis of a total amount of the aqueous ophthalmic composition.

In addition, the content proportion of zinc chloride based on the content of the terpenoid contained in the aqueous ophthalmic composition is not particularly limited, and, for example, zinc chloride is in an amount of from 0.000005 to 5,000 parts by weight, preferably from 0.0005 to 1,000 parts by weight, more preferably from 0.002 to 500 parts by weight, especially preferably from 0.002 to 10 parts by weight, and most preferably from 0.002 to 1 part by weight, based on 1 part by weight of a total amount of the component (A), i.e. a terpenoid, contained in the aqueous ophthalmic composition.

(3) At Least One Member Selected from the Group Consisting of Cellulose-Based Polymeric Compounds, Vinyl-Based Polymeric Compounds, Polyethylene Glycols and Dextran In the aqueous ophthalmic composition of the present invention, at least one member selected from the group consisting of cellulose-based polymeric compounds, vinyl-based polymeric compounds, polyethylene glycols and dextran (hereinafter also expressed as the component (C)) is contained at the same time, together with the terpenoid, i.e. the component (A), and zinc chloride, i.e. the component (B), whereby the adsorption of the terpenoid to the container is inhibited, so that the reduction in the content of the terpenoid in the aqueous ophthalmic composition can be inhibited over a long period of time. Further, the aqueous ophthalmic composition of the present invention has an excellent action such as an action for inhibiting histamine release or an action for inhibiting discharges from the eyes, so that some effects such as enhancement of anti-histamine action and inhibition of the amount of discharges from the eyes are exhibited by the use of the aqueous ophthalmic composition.

In the aqueous ophthalmic composition of the present invention, the component (C) can be used without particular limitations so long as the component is pharmacologically (pharmaceutically) or physiologically acceptable in the field of medicine.

The cellulose-based polymeric compounds used in the present invention can be exemplified by cellulose, cellulose derivatives in which a hydroxyl group of the cellulose is substituted by another functional group, salts thereof, and the like. In the cellulose derivative, the functional group substituting a hydroxyl group is not particularly limited, so long as the group is pharmacologically (pharmaceutically) or physiologically acceptable in the field of medicine. Concretely, the functional group includes an alkoxyl group having 1 to 5 carbon atoms, preferably 1 to 3 carbon atoms, which may be substituted with a hydroxyl group or a carboxyl group, preferably the number of substituents being 1, and concretely, the functional group is exemplified by a methoxy group, an ethoxy group, a hydroxymethoxy group, a hydroxyethoxy group, a hydroxypropoxy group, a carboxymethoxy group, a carboxyethoxy group, and the like. Concrete examples of the cellulose derivative include methyl cellulose, ethyl cellulose, hydroxyethyl cellulose, hydroxymethyl cellulose, hydroxypropyl cellulose, hydroxypropylmethyl cellulose (hypromellose), carboxymethyl cellulose, carboxymethyl cellulose sodium, carboxyethyl cellulose, and the like.

The salts of the cellulose and derivatives thereof are not particularly limited, so long as the salts are pharmacologically (pharmaceutically) or physiologically acceptable in the field of medicine. The salts can be exemplified by alkali metal salts such as sodium salts and potassium salts.

Among the cellulose-based polymeric compounds, hydroxypropylmethyl cellulose, hydroxyethyl cellulose, carboxymethyl cellulose, carboxymethyl cellulose sodium are preferred, and hydroxypropylmethyl cellulose and hydroxyethyl cellulose are more preferred.

As these cellulose-based polymeric compounds, commercially available products can be used. As the methyl cellulose, for example, those sold by Shin-Etsu Chemical Co., Ltd. as METOLOSE SM Series, including SM-15 (average molecular weight: about 70,000), SM-25 (average molecular weight: about 90,000), SM-50 (average molecular weight: about 110,000), SM-100 (average molecular weight: about 120,000), SM-400 (average molecular weight: about 170,000), SM-1500 (average molecular weight: about 290,000), SM-4000 (average molecular weight: about 360,000), and the like can be utilized. As the hydroxyethyl cellulose, for example, those sold by Sumitomo Seika Chemicals Co., Ltd., including HEC-CF-G (average molecular weight: about 400,000), HEC-CF-H (average molecular weight: about 700,000), HEC-CF-V (average molecular weight: about 1,000,000), HEC-CF-W (average molecular weight: about 1,300,000), HEC-CF-X (average molecular weight: about 1,500,000), HEC-CF-Y (average molecular weight: about 1,800,000), and the like can be utilized. The hydroxypropylmethyl cellulose includes, for example, Hydroxypropylmethyl Cellulose 2208, Hydroxypropylmethyl Cellulose 2906, Hydroxypropylmethyl Cellulose 2910, and the like, and those sold by Shin-Etsu Chemical Co., Ltd. as METOLOSE SH Series, including 60SH-15 (average molecular weight: about 70,000), 60SH-50 (average molecular weight: about 100,000), 60SH-4000 (average molecular weight: about 300,000), 60SH-10000 (average molecular weight: about 500,000), 65SH-50 (average molecular weight: about 100,000), 65SH-400 (average molecular weight: about 110,000), 65SH-1500 (average molecular weight: about 200,000), 65SH-4000 (average molecular weight: about 300,000), 65SH-150000 (average molecular weight: about 800,000), 90SH-4000 (average molecular weight: about 300,000), and the like can be utilized.

These cellulose-based polymeric compounds may be used as a single kind alone, or in a combination of two or more kinds. Especially, Hydroxypropylmethyl Cellulose 2906 or Hydroxypropylmethyl Cellulose 2910 is preferred.

The molecular weight of the cellulose-based polymeric compound may differ depending upon the kinds of substituents and degrees of substitution and the like, and the molecular weight is, in terms of weight-average molecular weight, of usually from 1,000 to 1,500,000, preferably from 5,000 to 1,300,000, and more preferably from 10,000 to 1,000,000 or so.

The vinyl-based polymeric compound used in the present invention refers to a polymer (vinyl-based polymer) obtained by polymerizing monomer compounds having a vinyl group, and optionally saponifying the polymer, or a salt thereof. The vinyl-based polymer are concretely exemplified by polyvinyl alcohol (perfectly or partially saponified products), polyvinyl pyrrolidone, and the like, and the polyvinyl pyrrolidone is preferred.

The molecular weight of the vinyl-based polymeric compound differs depending upon the kinds of the constituting monomers and the like, and those having a molecular weight, in terms of weight-average molecular weight, of usually from 1,000 to 2,500,000, preferably from 5,000 to 2,000,000, more preferably from 10,000 to 1,500,000 or so can be used.

More concretely, when the vinyl-based polymeric compound is a polyvinyl alcohol, the polyvinyl alcohol having an average degree of polymerization, measured as prescribed in JIS K-6726, of usually from 700 to 4,500, preferably from 800 to 4,000, more preferably from 900 to 3,500 or so, including, for example, those ranging from 900 to 1,100 or those ranging from 2,900 to 3,100, can be used.

In addition, the vinyl-based polymeric compound is a polyvinyl pyrrolidone, the polyvinyl pyrrolidone having a K value measured according to Fikentscher's method of usually from 15 to 100, preferably from 20 to 99, more preferably from 22 to 98 or so, including, for example, those ranging from 22 to 28 and those ranging from 87 to 93, can be used.

In addition, the salts of the vinyl-based polymeric compound are not particularly limited, so long as the salts are in the forms that are pharmacologically (pharmaceutically) or physiologically acceptable in the field of medicine, and the salts can be exemplified by salts with inorganic bases such as sodium salts and potassium salts, salts with organic bases such as triethanolamine salts, and the like.

As these vinyl-based polymeric compounds, commercially available products can be used. As the polyvinyl pyrrolidone, for example, those sold by BASF as Colidone Series, including Colidone 25 (average molecular weight: about 30,000), Colidone 30 (average molecular weight: about 50,000), Colidone 17PF (average molecular weight: about 90,000), Colidone 90 (average molecular weight: about 120,000), and the like can be utilized. As the polyvinyl alcohol, for example, those sold by The Nippon Synthetic Chemical Industry Co., Ltd. as Gohsenol Series, including Gohsenol EGOS (average molecular weight: about 30,000), Gohsenol EG40 (average molecular weight: about 120,000), and the like can be utilized. In addition, these vinyl-based polymeric compounds can be used as a single kind alone or in a combination of two or more kinds.

The dextran used in the present invention is a water-soluble polymeric compound obtained by partially hydrolyzing a polysaccharide produced by a certain kind of lactic acid bacteria using sucrose as a raw material. The dextran having a weight-average molecular weight of from 5,000 to 1,000,000, preferably from 10,000 to 500,000, and more preferably from 10,000 to 100,000 or so can be used. Among them, the dextran, Dextran 70 and Dextran 40 are preferred, and Dextran 70 is especially preferred, from the viewpoint of even more increasing the effects of the present invention. In addition, as the dextran, commercially available products can be used, and the dextran can be used alone or in a combination of two or more kinds.

The polyethylene glycol used in the present invention, which is also called macrogol, is not limited in the degree of substitutions of the substituents and molecular weights, and the polyethylene glycol having a weight-average molecular weight of from 100 to 50,000, preferably from 400 to 20,000, and more preferably from 2,000 to 10,000 or so can be used. Among them, Macrogol 6000, Macrogol 4000, and Macrogol 400 are preferred, and Macrogol 400 is especially preferred, from the viewpoint of even more increasing the effects of the present invention. In addition, as these polyethylene glycols commercially available products can be used, and the polyethylene glycols can be used alone or in combination of two or more kinds.

In the aqueous ophthalmic composition of the present invention, as the component (C), hydroxyethyl cellulose, hydroxypropylmethyl cellulose, carboxymethyl cellulose, carboxymethyl cellulose sodium, polyvinyl pyrrolidone, dextran, polyethylene glycol and the like are preferred, hydroxyethyl cellulose, hydroxypropylmethyl cellulose (hypromellose), polyvinyl pyrrolidone, and dextran are more preferred, and hydroxyethyl cellulose and hydroxypropylmethyl cellulose are especially preferred.

In the aqueous ophthalmic composition of the present invention, the content proportion of at least one kind of the component (C) selected from the group consisting of cellulose-based polymeric compounds, vinyl-based polymeric compounds, polyethylene glycols, and dextran to the content of the terpenoids is such that, for example, a total amount of the component (C) is preferably from 0.0005 to 1,000,000 parts by weight, more preferably from 0.05 to 10,000 parts by weight, even more preferably from 0.2 to 3,000 parts by weight, especially preferably from 0.5 to 1,000 parts by weight, and most preferably from 1 to 200 parts by weight, based on 1 part by weight of a total amount of the terpenoids.

In addition, the content proportion of the component (C) to the content of zinc chloride is such that, for example, a total amount of the component (C) is preferably from 0.002 to 100,000 parts by weight, more preferably from 0.5 to 60,000 parts by weight, even more preferably from 1 to 40,000 parts by weight, especially preferably from 2 to 30,000 parts by weight, and most preferably from 2 to 10,000 parts by weight, based on 1 part by weight of zinc chloride.

In the aqueous ophthalmic composition of the present invention, the content proportion of the component (C) in the aqueous ophthalmic composition is not particularly limited, and the content proportions can be properly determined depending upon concrete applications, methods of use of the aqueous ophthalmic composition. For example, a total amount of the component (C) is from 0.0001 to 25 w/v %, preferably from 0.001 to 10 w/v %, more preferably from 0.0025 to 10 w/v %, especially preferably from 0.01 to 5 w/v %, and most preferably from 0.01 to 2.5 w/v %, on the basis of a total amount of the aqueous ophthalmic composition. In addition, it is needless to say that the dose can be increased or decreased depending upon the number of doses, methods of administration, and the like.

Here, within the range of the content proportion of a total amount of the component (C) mentioned above, the content proportion of the cellulose-based polymeric compound is from 0.0001 to 10 w/v %, preferably from 0.0025 to 7 w/v %, more preferably from 0.005 to 5 w/v %, especially preferably from 0.01 to 3 w/v %, and most preferably from 0.05 to 2.5 w/v % or so, on the basis of a total amount of the aqueous ophthalmic composition. The content proportion of the vinyl-based polymeric compound is from 0.0001 to 10 w/v %, preferably from 0.0025 to 7 w/v %, more preferably from 0.005 to 5 w/v %, especially preferably from 0.01 to 3 w/v %, and most preferably from 0.05 to 2.5 w/v % or so, on the basis of a total amount of the aqueous ophthalmic composition. The content proportion of the dextran is from 0.001 to 25 w/v %, preferably from 0.001 to 10 w/v %, more preferably from 0.01 to 10 w/v %, even more preferably from 0.01 to 5 w/v %, especially preferably from 0.01 to 1 w/v %, and more especially preferably from 0.01 to 0.1 w/v %, on the basis of a total amount of the aqueous ophthalmic composition. The content proportion of the polyethylene glycol is from 0.001 to 25 w/v %, preferably from 0.001 to 10 w/v %, more preferably from 0.01 to 10 w/v %, even more preferably from 0.05 to 5 w/v %, and especially preferably from 0.05 to 2 w/v %, on the basis of a total amount of the aqueous ophthalmic composition.

(4) Surfactant

The aqueous ophthalmic composition of the present invention contains the components (A) to (C) mentioned above, and can optionally contain a surfactant. Since the aqueous ophthalmic composition contains a surfactant, the effects of the present invention, in other words, the effects such as inhibition of adsorption of the terpenoid to the container, enhancement of inhibitory action for histamine release, and inhibition of discharges from the eyes are more remarkably exhibited.

The surfactant which can be contained in the aqueous ophthalmic composition of the present invention is not particularly limited, with the limit of being phaiinacologically (pharmaceutically) or physiologically acceptable in the field of medicine, and the surfactant may be any one of nonionic surfactants, amphoteric surfactants, anionic surfactants, and cationic surfactants. Since the aqueous ophthalmic composition contains a surfactant, the effects of the present invention can be more remarkably exhibited.

Among them, concrete examples of the nonionic surfactants include POE sorbitan fatty acid esters such as POE(20) sorbitan monolaurate (Polysorbate 20), POE(20) sorbitan. monopalmitate (Polysorbate 40), POE(20) sorbitan monostearate (Polysorbate 60), POE(20) sorbitan tristearate (Polysorbate 65), and POE(20) sorbitan monooleate (Polysorbate 80); POE-POP block copolymers such as Poloxamer 407, Poloxamer 235, Poloxamer 188, Poloxamer 403, Poloxamer 237, and Poloxamer 124; POE hydrogenated castor oils such as POE(60) hydrogenated castor oil (polyoxyethylene hydrogenated castor oil 60); POE alkyl ethers such as POE(9) lauryl ether; POE-POP alkyl ethers such as POE (20)POP(4) cetyl ether; POE alkyl phenyl ethers such as POE(10) nonyl phenyl ethers; and the like. Here, in the compounds exemplified above, POE stands for polyoxyethylene, POP stands for polyoxypropylene, and the numbers inside parentheses stand for the number of moles added. In addition, the amphoteric surfactants which can be contained in the aqueous ophthalmic composition of the present invention are concretely exemplified by alkyldiaminoethyl glycines, and the like. In addition, the cationic surfactants which can be contained in the aqueous ophthalmic composition of the present invention are concretely exemplified by benzalkonium chloride, benzethonium chloride, and the like. Also, the anionic surfactants which can be contained in the aqueous ophthalmic composition of the present invention are concretely exemplified by alkylbenzenesulfonates, alkyl sulfates, polyoxyethylene alkyl sulfates, α-sulfomethyl esters of fatty acids, α-olefinsulfonates, and the like.

In the aqueous ophthalmic composition of the present invention, the surfactants may be used in a single kind alone or in a combination of two or more kinds.

The content proportion of the surfactant in the aqueous ophthalmic composition of the present invention is not particularly limited, and as one embodiment, the content proportion of the surfactant in a total amount is preferably from 0.001 to 5 w/v %, more preferably from 0.01 to 1 w/v %, and even more preferably from 0.03 to 0.5 w/v %, on the basis of a total amount of the aqueous ophthalmic composition.

More specifically, the following content proportions are exemplified.

In a case where the surfactant is a nonionic surfactant, the content proportion of the nonionic surfactant in a total amount is preferably from 0.001 to 2 w/v %, more preferably from 0.01 to 1 w/v %, and even more preferably from 0.03 to 0.5 w/v %, on the basis of a total amount of the aqueous ophthalmic composition.

In a case where the surfactant is an amphoteric surfactant, the content proportion of the amphoteric surfactant in a total amount is preferably from 0.001 to 1 w/v %, more preferably from 0.005 to 0.5 w/v %, and even more preferably from 0.01 to 0.1 w/v %, on the basis of a total amount of the aqueous ophthalmic composition.

In a case where the surfactant is an anionic surfactant, the content proportion of the anionic surfactant in a total amount is preferably from 0.001 to 2 w/v %, more preferably from 0.01 to 1 w/v %, and even more preferably from 0.03 to 0.5 w/v %, on the basis of a total amount of the aqueous ophthalmic composition.

In a case where the surfactant is a cationic surfactant, the content proportion of the cationic surfactant in a total amount is preferably from 0.001 to 1 w/v %, more preferably from 0.005 to 0.5 w/v %, and even more preferably from 0.01 to 0.1 w/v %, on the basis of a total amount of the aqueous ophthalmic composition.

(5) Other Components

The aqueous ophthalmic composition of the present invention contains the component (A), the component (B), and the component (C) mentioned above, and the aqueous ophthalmic composition can selectively contain various pharmacologically active components and physiologically active components according to the conventional methods, depending upon the applications and formulation forms thereof, within the range that would not impair the effects of the present invention.

Further, the aqueous ophthalmic composition of the present invention can contain various additives according to the conventional methods, depending upon the applications and formulation forms thereof, within the range that would not impair the effects of the present invention.

(6) pH of Aqueous Ophthalmic Composition

According to the aqueous ophthalmic composition of the present invention, since in the aqueous composition containing the terpenoid, at least one member selected from the group consisting of cellulose-based polymeric compounds, vinyl-based polymeric compounds, polyethylene glycols and dextran is combined together with zinc chloride, adsorption of the terpenoid to a container can be inhibited over a wide pH range, and further gives actions such as enhancement of inhibitory effects for histamine release and inhibition of discharges from the eyes. Therefore, the pH value of the aqueous ophthalmic composition of the present invention is not particularly limited, so long as it is pharmacologically (pharmaceutically) or physiologically acceptable in the field of medicine, which can be properly determined depending upon concrete applications, formulation forms, methods of use, and the like of the aqueous ophthalmic composition. One embodiment of a pH of the aqueous ophthalmic composition of the present invention includes ranges from 3.5 to 9.5, preferably from 3.8 to 9.0, more preferably from 4.2 to 8.8, even more preferably from 4.5 to 8.5, and especially preferably from 5.0 to 8.0.

(7) Method of Preparation and Applications of Aqueous Ophthalmic Composition

The aqueous ophthalmic composition of the present invention may be any aqueous composition containing (A) a terpenoid, (B) zinc chloride, and (C) at least one member selected from the group consisting of cellulose-based polymeric compounds, vinyl-based polymeric compounds, polyethylene glycols and dextran, and a production method thereof is not particularly limited, and the aqueous composition can be prepared according to a method known to one of ordinary skill in the art. For example, the aqueous composition can be produced by dissolving each of the components in a proper amount of purified water, thereafter adjusting to a given pH value, and subsequently adding the remaining purified water to adjust its volume. In addition, the aqueous composition may also be optionally subjected to filtration and sterilization treatment, and then filled to the container.

Therefore, from another aspect, the present invention provides a method for producing an aqueous ophthalmic composition having an action of inhibiting adsorption of the terpenoid to a container, an enhanced inhibitory action for histamine release, and an inhibitory action for discharges from the eyes, including adding (A) a terpenoid, (B) zinc chloride, and (C) at least one member selected from the group consisting of cellulose-based polymeric compounds, vinyl-based polymeric compounds, polyethylene glycols and dextran to a carrier containing water.

The aqueous ophthalmic composition of the present invention can be used as formulations such as medicaments and quasi-drugs, including eye drops [the eye drops including eye drops which can be instilled into the eyes while wearing contact lenses], artificial tears, eyewashes [the eyewashes including eyewashes which can wash the eyes while wearing contact lenses], compositions for contact lenses [solutions for wearing contact lenses, compositions for contact lenses care (disinfectant solutions for contact lens, storage solutions for contact lens, cleansing solutions for contact lenses, cleansing-storage solutions for contact lenses), and the like], and the like. One preferred example of the aqueous ophthalmic composition of the present invention includes eye drops, artificial tears, eyewashes, and solutions for wearing contact lenses, and especially preferred example includes eye drops and artificial tears. Here, when used as compositions for contact lenses, the aqueous ophthalmic composition is applicable to all sorts of contact lenses, including hard contact lenses and soft contact lenses.

The aqueous ophthalmic composition of the present invention can be provided by housing the aqueous ophthalmic composition in any sorts of containers. The container for housing the aqueous ophthalmic composition of the present invention is not particularly limited, and any container made of materials that can be used in a general container in the field of the art may be used, and, for example, glass materials and plastic materials, e.g. polyethylene terephthalate resin, polypropylene resin, polyethylene resin, polyethylene naphthalate resin, and the like, may be properly selected and used according to their purposes and applications. In addition, the container for housing the aqueous ophthalmic composition of the present invention may be a transparent container in which the internal of the container can be visually recognized, or an opaque container which is difficult to visually recognize the internal. Since the confirmation of the amount of the solution of the aqueous ophthalmic composition, foreign objects tests during the production steps, and the like is facilitated, especially transparent containers are preferred. Here, the term "transparent container" includes both colorless transparent containers and colored transparent containers.

The aqueous ophthalmic composition of the present invention can especially remarkably inhibit the reduction in the content of the terpenoid by adsorption of the terpenoid to the container, even when the aqueous ophthalmic composition is housed in a plastic container which is more likely to cause adsorption of the terpenoid in the conventional aqueous ophthalmic composition. For this reason, the aqueous ophthalmic composition of the present invention is highly useful as an aqueous ophthalmic composition used after housing in a plastic container, and especially highly useful as an aqueous ophthalmic composition housed in a container made of a material including a polyethylene terephthalate resin or polyethylene resin to which terpenoid is more likely to be adsorbed.

Further, the aqueous ophthalmic composition of the present invention is provided not only as a package form of "fully use at once" type, but also is useful as an aqueous ophthalmic composition of multi-dose which is a package in the form that is administered over plural times, and the user continuously doses.

2. Method for Inhibiting Adsorption of Terpenoid in Aqueous Ophthalmic Composition to Container As mentioned above, since in the aqueous ophthalmic composition (B) zinc chloride and (C) at least one member selected from the group consisting of cellulose-based polymeric compounds, vinyl-based polymeric compounds, polyethylene glycols and dextran are combined together with (A) a terpenoid, the terpenoid contained in the aqueous ophthalmic composition can be inhibited from being adsorbed to a container, such as a plastic container, especially a container made of polyethylene terephthalate, thereby inhibiting the reduction in the terpenoid content in the aqueous ophthalmic composition.

Therefore, the present invention provides a method for inhibiting adsorption of the terpenoid in the aqueous ophthalmic composition to a container, or a method for inhibiting the reduction in the content of the terpenoid, including combining in the aqueous ophthalmic composition of the present invention (B) zinc chloride and (C) at least one member selected from the group consisting of cellulose-based polymeric compounds, vinyl-based polymeric compounds, polyethylene glycols and dextran, together with (A) a terpenoid.

Further, from another aspect, the present invention provides use of (A) a terpenoid, (B) zinc chloride, and (C) at least one member selected from the group consisting of cellulose-based polymeric compounds, vinyl-based polymeric compounds, polyethylene glycols and dextran, in the manufacture of an aqueous ophthalmic composition having an action for inhibiting adsorption of the terpenoid to a container.

Further, from another aspect, the present invention provides use of a composition containing (A) a terpenoid, (B) zinc chloride, and (C) at least one member selected from the group consisting of cellulose-based polymeric compounds, vinyl-based polymeric compounds, polyethylene glycols and dextran, as an aqueous ophthalmic composition having an action for inhibiting adsorption of the terpenoid to a container.

Further, from another aspect, the present invention provides a composition containing (A) a terpenoid, (B) zinc chloride, and (C) at least one member selected from the group consisting of cellulose-based polymeric compounds, vinyl-based polymeric compounds, polyethylene glycols and dextran, for use in an aqueous ophthalmic composition having an action for inhibiting adsorption of the terpenoid to a container.

In these methods, use, and compositions, the component (A), the component (B), and the component (C) may be co-present in an aqueous ophthalmic composition, and the order of addition of those components are not particularly limited. The components (A) to (C) may be those that can be combined in the aqueous ophthalmic composition of the present invention, and amounts thereof may be amount that can be combined in the aqueous ophthalmic composition of the present invention. Also, the kinds and contents of each of the components combined in the aqueous ophthalmic composition, the kinds and contents of the other components combined, formulation forms of the composition, and the like are the same as the aqueous ophthalmic composition of the present invention.

3. Method for Enhancing Inhibitory Action for Histamine Release and Method for Inhibiting or Treating Itchiness of the Eyes Further, as mentioned above, by providing an aqueous ophthalmic composition containing (A) a terpenoid, (B) zinc chloride, and (C) at least one member selected from the group consisting of cellulose-based polymeric compounds, vinyl-based polymeric compounds, polyethylene glycols and dextran, inhibitory action for histamine release in the aqueous ophthalmic composition can be enhanced.

Accordingly, from another aspect, the present invention provides a method for enhancing inhibitory action for histamine release of an aqueous ophthalmic composition, including combining in the aqueous ophthalmic composition (A) a terpenoid, (B) zinc chloride, and (C) at least one member selected from the group consisting of cellulose-based polymeric compounds, vinyl-based polymeric compounds, polyethylene glycols and dextran.

Further, from another aspect, the present invention provides use of (A) a terpenoid, (B) zinc chloride, and (C) at least one member selected from the group consisting of cellulose-based polymeric compounds, vinyl-based polymeric compounds, polyethylene glycols and dextran, in the manufacture of an aqueous ophthalmic composition having an enhanced inhibitory action for histamine release.

Further, from another aspect, the present invention provides use of a composition containing (A) a terpenoid, (B) zinc chloride, and (C) at least one member selected from the group consisting of cellulose-based polymeric compounds, vinyl-based polymeric compounds, polyethylene glycols and dextran, as an aqueous ophthalmic composition having an enhanced inhibitory action for histamine release.

Further, from another aspect, the present invention provides a composition containing (A) a terpenoid, (B) zinc chloride, and (C) at least one member selected from the group consisting of cellulose-based polymeric compounds, vinyl-based polymeric compounds, polyethylene glycols and dextran, for use in an aqueous ophthalmic composition having an enhanced inhibitory action for histamine release.

In addition, as mentioned above, by contacting the aqueous ophthalmic composition of the present invention with the cornea and/or conjunctiva by a method such as eye dropping or washing eyes using the composition as eye drops or eyewashes, the action for inhibiting histamine release is enhanced, and whereby consequently anti-histamine action is enhanced, so that itchiness of the eyes can be inhibited or treated.

Therefore, further, from another aspect, the present invention provides a method for inhibiting or treating itchiness of the eyes, including contacting an aqueous ophthalmic composition containing (A) a terpenoid, (B) zinc chloride, and (C) at least one member selected from the group consisting of cellulose-based polymeric compounds, vinyl-based polymeric compounds, polyethylene glycols and dextran, with the cornea and/or conjunctiva.

In these methods, use, and compositions, (A) a terpenoid, (B) zinc chloride, and (C) at least one member selected from the group consisting of cellulose-based polymeric compounds, vinyl-based polymeric compounds, polyethylene glycols and dextran may be co-present in the aqueous ophthalmic composition, and the order of addition of those components are not particularly limited. (A) A terpenoid, (B) zinc chloride, and (C) at least one member selected from the group consisting of cellulose-based polymeric compounds, vinyl-based polymeric compounds, polyethylene glycols and dextran may be those that can be combined in the aqueous ophthalmic composition of the present invention, and amounts thereof may be amounts that can be combined in the aqueous ophthalmic composition of the present invention. Also, the kinds and contents of each of the components to be combined in the aqueous ophthalmic composition, the kinds and contents of the other components to be combined, formulation forms of the composition, and the like are the same as the aqueous ophthalmic composition of the present invention.

4. Method for Inhibiting Discharges from the Eyes

Further, as mentioned above, by providing an aqueous ophthalmic composition containing (A) a terpenoid, (B) zinc chloride, and (C) at least one member selected from the group consisting of cellulose-based polymeric compounds, vinyl-based polymeric compounds, polyethylene glycols and dextran, an action for inhibiting discharges from the eyes can be given to the aqueous ophthalmic composition.

Accordingly, from another aspect, the present invention provides a method for providing an action for inhibiting discharges from the eyes to an aqueous ophthalmic composition, including combining in the aqueous ophthalmic composition (A) a terpenoid, (B) zinc chloride, and (C) at least one member selected from the group consisting of cellulose-based polymeric compounds; vinyl-based polymeric compounds, polyethylene glycols and dextran.

Further, from another aspect, the present invention provides use of (A) a terpenoid, (B) zinc chloride, and (C) at least one member selected from the group consisting of cellulose-based polymeric compounds, vinyl-based polymeric compounds, polyethylene glycols and dextran, in the manufacture of an aqueous ophthalmic composition having an inhibitory action for discharges from the eyes.

Further, from another aspect, the present invention provides use of a composition containing (A) a terpenoid, (B) zinc chloride, and (C) at least one member selected from the group consisting of cellulose-based polymeric compounds, vinyl-based polymeric compounds, polyethylene glycols and dextran, as an aqueous ophthalmic composition having an inhibitory action for discharges from the eyes.

Further, from another aspect, the present invention provides a composition containing (A) a terpenoid, (B) zinc chloride, and (C) at least one member selected from the group consisting of cellulose-based polymeric compounds, vinyl-based polymeric compounds, polyethylene glycols and dextran, for use in an aqueous ophthalmic composition having an inhibitory action for discharges from the eyes.

In addition, as mentioned above, by contacting an aqueous ophthalmic composition of the present invention with the cornea and/or conjunctiva by a method such as eye dropping or washing eyes using the composition as eye drops or eyewashes, the discharges from the eyes can be inhibited, so that ease in opening eyes, ease in blinking, blurriness of eyes, appreciative appearance or the like can be ameliorated.

Therefore, further, from another aspect, the present invention provides a method for inhibiting discharges from the eyes, including contacting an aqueous ophthalmic composition containing (A) a terpenoid, (B) zinc chloride, and (C) at least one member selected from the group consisting of cellulose-based polymeric compounds, vinyl-based polymeric compounds, polyethylene glycols and dextran, with the cornea and/or conjunctiva.

In these methods, use, and compositions, so long as (A) a terpenoid, (B) zinc chloride, and (C) at least one member selected from the group consisting of cellulose-based polymeric compounds, vinyl-based polymeric compounds, polyethylene glycols and dextran are co-present in the aqueous ophthalmic composition, the order of addition of those components is not particularly limited. (A) A terpenoid, (B) zinc chloride, and (C) at least one member selected from the group consisting of cellulose-based polymeric compounds, vinyl-based polymeric compounds, polyethylene glycols and dextran may be those that can be combined in the aqueous ophthalmic composition of the present invention, and amounts thereof may be amount that can be combined, in the aqueous ophthalmic composition of the present invention. Also, the kinds and contents of each of the components to be combined in the aqueous ophthalmic composition, the kinds and contents of the other components to be combined, formulation forms of the composition, and the like are the same as the aqueous ophthalmic composition of the present invention.

EXAMPLES

The present invention will be described in detail hereinbelow by means of Examples and Test Examples, without intending to limit the present invention to these Examples and the like.

Test Example 1

Each of the aqueous ophthalmic compositions of Comparative Example 1 and Examples 1 to 3 having a composition as listed in Table 1 was prepared, and 8 mL each was dispensed in a 10 mL eye drop container made of polyethylene terephthalate (hereinafter also referred to as "PET"), and a nozzle made of polyethylene (hereinafter also referred to as "PE") and a cap were fitted thereto. The units for the content proportions of the components in Table 1 are w/v %.

Next, these containers were allowed to stand in a thermostat held at 50° C. for one week. Here, "allowed (allowing) to stand" refers to a state of allowing to stand without applying shaking. The content of the 1-menthol in the test solution immediately after the preparation and the content after allowing the test solution to stand at 50° C. for one week were measured according to a conventional method using gas chromatography.

Based on the measurement results, the rate of adsorption of 1-menthol in the test solution and the rate of inhibiting adsorption of the 1-menthol were calculated in accordance with the following formulas (1) to (3). The results are also together shown in the following Table 1.

$$\text{Residual Rate (\%)} = \frac{\text{1-Menthol Content After Allowing to Stand at 50° C. for One Week}}{\text{1-Menthol Content Immediately After the Preparation}} \times 100 \quad \text{formula (1)}$$

$$\text{Rate of Adsorption of 1-Menthol to the Container (\%)} = 100\ (\%) - \text{Residual Rate (\%)} \quad \text{formula (2)}$$

$$\text{Rate of Inhibiting Adsorption (\%) of 1-Menthol (\%)} = \frac{\text{Rate of Adsorption (\%) of Comparative Example 1} - \text{Rate of Adsorption (\%)}}{\text{Rate of Adsorption (\%) of Comparative Example 1}} \times 100 \quad \text{formula (3)}$$

TABLE 1

|  | Comp. Ex. 1 | Ex. 1 | Ex. 2 | Ex. 3 |
|---|---|---|---|---|
| Zinc Chloride | — | 0.01 | 0.01 | 0.01 |
| 1-Menthol | 0.015 | 0.015 | 0.015 | 0.015 |
| Polysorbate 80 | 0.05 | 0.05 | 0.05 | 0.05 |
| Hydroxypropylmethyl Cellulose | — | 0.2 | — | — |
| Carboxymethyl Cellulose Sodium | — | — | 0.2 | — |
| Polyethylene Glycol 400 | — | — | — | 0.2 |
| Hydrochloric Acid | q.s. | q.s. | q.s. | q.s. |
| Sodium Hydroxide | q.s. | q.s. | q.s. | q.s. |
| Purified Water | q.s. | q.s. | q.s. | q.s. |
| pH (r.t.) | 7 | 7 | 7 | 7 |
| Viscosity (mPa · s, measured at 20° C.) | 1.0 | 3.6 | 10.8 | 1.1 |
| Rate of Adsorption of 1-Menthol to Container (%) | 14.8 | 11.4 | 2.4 | 11.0 |
| Rate of Inhibiting Adsorption of 1-Menthol (%) | — | 22.6 | 83.6 | 25.8 |

Units of the content proportions of the components being w/v %.

As is clear from the results of Comparative Example 1 and Examples 1 to 3 in Table 1, in cases where in the aqueous ophthalmic compositions containing 1-menthol, hydroxypropylmethyl cellulose, carboxymethyl cellulose sodium or polyethylene glycol 400 was combined together with zinc chloride (Examples 1 to 3), the rate of adsorption of 1-menthol was greatly lowered, so that the effect of inhibiting adsorption was improved.

Test Example 2

Each of the aqueous ophthalmic aqueous compositions having a composition as listed in Table 2 of Comparative Example 1, Comparative Example 2, Example 1, and Examples 3 to 5 was prepared, and 8 mL each was dispensed in a 10 mL eye drop container made of PET, and a nozzle (made of PE) and a cap were fitted thereto.

TABLE 2

|  | Comp. Ex. 1 | Ex. 1 | Ex. 3 | Ex. 4 | Ex. 5 | Comp. Ex. 2 |
|---|---|---|---|---|---|---|
| Zinc Chloride | — | 0.01 | 0.01 | 0.01 | 0.01 | — |
| Zinc Sulfate | — | — | — | — | — | 0.01 |
| 1-Menthol | 0.015 | 0.015 | 0.015 | 0.015 | 0.015 | 0.015 |
| Polysorbate 80 | 0.05 | 0.05 | 0.05 | 0.05 | 0.05 | 0.05 |
| Hydroxypropylmethyl Cellulose | — | 0.2 | — | — | — | 0.2 |
| Polyvinyl Pyrrolidone | — | — | — | 0.2 | — | — |
| Dextran 70 | — | — | — | — | 0.2 | — |
| Polyethylene Glycol 400 | — | — | 0.2 | — | — | — |
| Hydrochloric Acid | q.s. | q.s. | q.s. | q.s. | q.s. | q.s. |
| Sodium Hydroxide | q.s. | q.s. | q.s. | q.s. | q.s. | q.s. |
| Purified Water | q.s. | q.s. | q.s. | q.s. | q.s. | q.s. |
| pH (r.t.) | 7 | 7 | 7 | 7 | 7 | 7 |
| Viscosity (mPa · s, measured at 20° C.) | 1.0 | 3.6 | 1.1 | 1.1 | 1.1 | 3.6 |

Units of the content proportions of the components being w/v %.

Next, these containers were allowed to stand in a thermostat held at 60° C. for one week. The content of the 1-menthol in the test solution immediately after the preparation and the content after allowing the test solution to stand at 60° C. for one week were measured according to a conventional method using gas chromatography.

Figure 1:
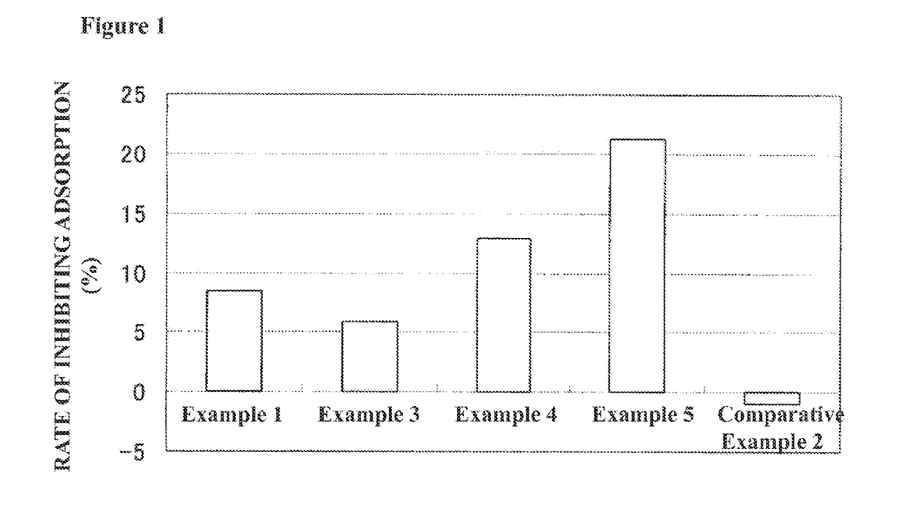
[FIG. 1] A graph showing the calculation results of the rate of inhibiting adsorption in Example 2.

Based on the found values, the residual rate and the rate of inhibiting adsorption of the 1-menthol in the test solution were calculated in accordance with the formulas (2) and (3) in Test Example 1, and the following foimula (4). FIG. 1 shows the calculation results of the rate of inhibiting adsorption.

$$\text{Residual Rate (\%)} = \frac{\text{1-Menthol Content After Allowing to Stand at 60° C. for one week}}{\text{1-Menthol Content Immedieatly After the Preperation}} \times 100 \quad \text{formula (4)}$$

Since hydroxypropylmethyl cellulose, polyvinyl pyrrolidone, Dextran 70 or Polyethylene Glycol 400, was combined together with zinc chloride in the aqueous ophthalmic composition containing 1-menthol, the adsorption of 1-menthol to the container was markedly inhibited (Examples 1, 3, 4, and 5).

On the other hand, the test solution of Comparative Example 2 in which the aqueous composition containing zinc sulfate in place of zinc chloride of Example 1 did not inhibit the adsorption of 1-menthol to the container but rather increased the amount of 1-menthol adsorbed to the container.

From these results, it was clarified that in cases where the cellulose-based polymeric compound, the vinyl-based polymeric compound, the polyethylene glycol or the dextran was used together with zinc chloride, the adsorption of 1-menthol to the container was inhibited, while a case where zinc sulfate was contained in place of zinc chloride (Comparative Example 2) rather increased adsorption of 1-menthol.

Therefore, it was clarified that the effect by the composition of the present invention of inhibiting adsorption of 1-menthol to the container is a peculiar effect when zinc chloride was used as a zinc compound.

Test Example 3

Each of the aqueous ophthalmic compositions of Comparative Examples 3 to 5 and Examples 6 to 7 having a composition as listed in Table 3 was prepared, and 8 mL each was dispensed in a 10 mL container made of PET, and a nozzle (made of PE) and a cap were fitted thereto.

TABLE 3

|  | Comp. Ex. 3 | Ex. 6 | Ex. 7 | Comp. Ex. 4 | Comp. Ex. 5 |
|---|---|---|---|---|---|
| Zinc Chloride | — | 0.01 | 0.01 | — | 0.01 |
| Zinc Sulfate | — | — | — | 0.01 | — |
| 1-Menthol | 0.015 | 0.015 | 0.015 | 0.015 | 0.015 |
| Polysorbate 80 | 0.05 | 0.05 | 0.05 | 0.05 | 0.05 |
| Hydroxypropylmethyl Cellulose | — | — | 0.2 | 0.2 | — |
| Hydroxyethyl Cellulose | — | 0.2 | — | — | — |
| Xanthan Gum | — | — | — | — | 0.2 |
| Hydrochloric Acid | q.s. | q.s. | q.s. | q.s. | q.s. |
| Sodium Hydroxide | q.s. | q.s. | q.s. | q.s. | q.s. |
| Purified Water | q.s. | q.s. | q.s. | q.s. | q.s. |
| pH (r.t.) | 6.5 | 6.5 | 6.5 | 6.5 | 6.5 |
| Viscosity (mPa · s, measured at 20° C.) | 1.0 | 4.3 | 3.6 | 3.6 | 278 |

*Units of the content proportions of the components being w/v %.

Next, the containers were allowed to stand in a thermostat held at 50° C. for one week. The content of the 1-menthol in the test solution immediately after the preparation and the content after allowing the test solution to stand at 50° C. for one week were measured according to a conventional method using gas chromatography.

Figure 2:
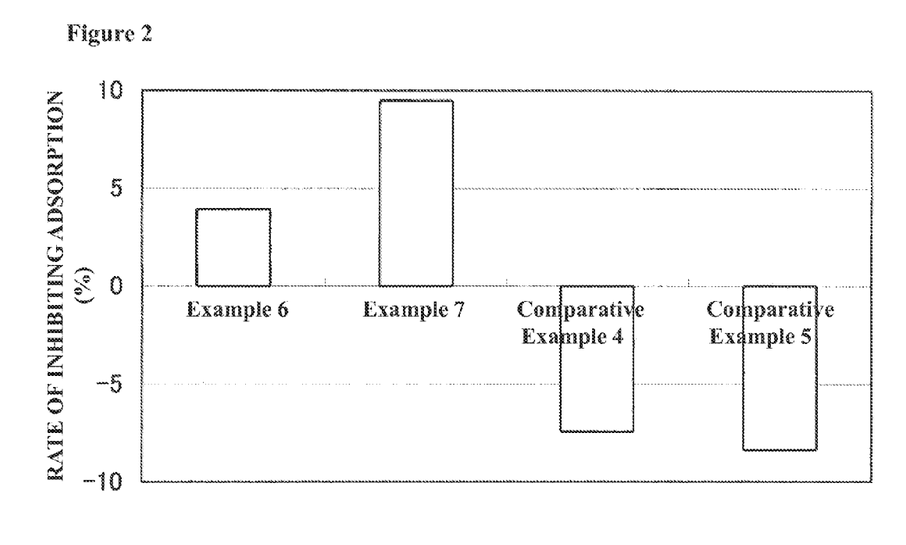
[FIG. 2] A graph showing the calculation results of the rate of inhibiting adsorption in Example 3.

Based on the measurement results, the rate of inhibiting adsorption of the 1-menthol in the test solution was calculated in accordance with the formulas (1) and (2) in Test Example 1, and the following formula (5). FIG. 2 shows the calculation results of the rate of inhibiting adsorption.

$$\text{Rate of Inhibiting Adsorption of 1-Menthol (\%)} = \frac{\text{Rate of Adsorption (\%) of Comparative Example 3} - \text{Rate of Adsorption (\%)}}{\text{Rate of Adsorption (\%) of Comparative Example 3}} \times 100 \quad \text{formula (5)}$$

Since zinc chloride, and hydroxypropylmethyl cellulose or hydroxyethyl cellulose are combined in the aqueous ophthalmic composition containing 1-menthol, the adsorption of 1-menthol to a container was markedly inhibited (Examples 6 and 7). By contrast, in Comparative Example 4 in which zinc sulfate was contained in place of zinc chloride in Example 7, the adsorption of 1-menthol to a container was not inhibited, but the adsorption of 1-menthol to a container rather increased. In addition, in the test solution of Comparative Example 5 in which xanthan gum, a thickening agent, was contained in place of hydroxyethyl cellulose combined to the test solution of Example 6 and hydroxypropylmethyl cellulose combined to the test solution of Example 7, the adsorption of 1-menthol to a container was not inhibited, but the adsorption of 1-menthol to a container rather increased.

It could be confirmed from these results that the aqueous ophthalmic composition in which zinc chloride was used as a zinc compound was further used together with a specified component such as a cellulose-based polymeric compound, a vinyl-based polymeric compound, polyethylene glycol, or dextran, whereby an effect of inhibiting the adsorption 1-menthol to a container was remarkably exhibited.

Test Example 4

Each of the aqueous ophthalmic compositions of Comparative Examples 6 to 7 and Example 8 having a composition as listed in Table 4 was prepared, and 8 mL each was dispensed in a 10 mL container made of polyethylene (PE), and a nozzle (made of PE) and a cap were fitted thereto.

TABLE 4

| | Comp. Ex. 6 | Comp. Ex. 7 | Ex. 8 |
|---|---|---|---|
| Zinc Chloride | — | 0.01 | 0.01 |
| 1-Menthol | 0.015 | 0.015 | 0.015 |
| Polysorbate 80 | 0.05 | 0.05 | 0.05 |
| Hydroxypropylmethyl Cellulose | — | — | 0.2 |
| Hydrochloric Acid | q.s. | q.s. | q.s. |
| Sodium Hydroxide | q.s. | q.s. | q.s. |
| Purified Water | q.s. | q.s. | q.s. |
| pH (r.t.) | 6.5 | 6.5 | 6.5 |

*Units of the content proportions of the components being w/v %.

Next, the containers were allowed to stand in a thermostat held at each of the temperatures of 50° C. and 60° C. for one week. The content of the 1-menthol in the test solution immediately after the preparation and the content after allowing the test solution to stand at 50° C. or 60° C. for one week were measured according to a conventional method using gas chromatography.

As a result, it was clarified that even in a case of filling the test solution in the eye drops container made of PE, the content of the 1-menthol after allowing the test solution to stand at 50° C. or 60° C. for one week was significantly higher in the test solution of Example 8 in which zinc chloride and hydroxypropylmethyl cellulose were contained at the same time, as compared to the test solution of Comparative Example 6 that did not contain zinc chloride and hydroxypropylmethyl cellulose, and the test solution of Comparative Example 7 that did not contain hydroxypropylmethyl cellulose, so that the adsorption of the 1-menthol was inhibited even in a container made of PE.

Test Example 5 (Inhibition for Adsorption of Terpenoid)

Test solutions were prepared in accordance with a formulation as listed in Table 5, the content of a terpenoid (1-menthol or d-borneol) was measured in the same manner as in Test Example 1, and the residual rate of the terpenoid in the test solution was calculated in accordance with the formula (4). In addition, the rate of inhibiting adsorption of the terpenoid to a container was calculated in accordance with the formula (2) and the following fon ula (6). The results are also shown together in Table 5.

The phrase "Corresponding Comparative Examples" as used herein concretely refers to an aqueous ophthalmic composition which does not contain a zinc compound, but a composition of all other components and pH are identical, or refers to an aqueous ophthalmic composition which does not contain a zinc compound and a component (C), but a composition of all other components and pH are identical. Concretely, one that corresponds to Example 9 is Comparative Example 8, one that corresponds to Example 10 is Comparative Example 9, and one that corresponds to Example 11 is Comparative Example 10.

$$\text{Rate of Inhibiting Adsorption of Terpenoid (\%)} = \left\{ 1 - \frac{\text{Rate of Adsorption (\%) of Example}}{\text{Rate of Adsorption (\%) of Corresponding Comparative Example}} \right\} \times 100 \quad \text{formula (6)}$$

TABLE 5

| Test Solution Name | Comp. Ex. 8 | Comp. Ex. 9 | Comp. Ex. 10 | Ex. 9 | Ex. 10 | Ex. 11 |
|---|---|---|---|---|---|---|
| Zinc Chloride | — | — | — | 0.0001 | 0.0005 | 0.008 |
| 1-Menthol | 0.015 | — | 0.01 | 0.015 | — | 0.01 |
| d-Borneol | — | 0.005 | — | — | 0.005 | — |
| Polysorbate 80 | 0.05 | 0.05 | 0.04 | 0.05 | 0.05 | 0.04 |
| Hypromellose | — | — | — | 0.6 | — | — |
| Hydroxyethyl Cellulose | — | 1 | 0.01 | — | 1 | 0.01 |
| Hydrochloric Acid | q.s. | q.s. | q.s. | q.s. | q.s. | q.s. |
| Sodium Hydroxide | q.s. | q.s. | q.s. | q.s. | q.s. | q.s. |
| Purified Water | Bal. | Bal. | Bal. | Bal. | Bal. | Bal. |
| pH | 7.8 | 7.8 | 7.8 | 7.8 | 7.8 | 7.8 |
| Rate of Inhibiting Adsorption (%) | — | — | — | 20.8 | 12.7 | 3.1 |

Units of the content proportions of the components being w/v %.

As is clear from Table 5, the aqueous ophthalmic composition containing zinc chloride, a terpenoid, and a component (C) (hypromellose or hydroxyethyl cellulose) (Examples 9 to 11) remarkably inhibited adsorption of the 1-menthol to a container, as compared to the aqueous ophthalmic composition containing a terpenoid without containing zinc chloride (Comparative Example 8), and the aqueous ophthalmic composition containing a terpenoid and a component (C) (hypromellose or hydroxyethyl cellulose) without containing zinc chloride (Comparative Examples 9 and 10).

Test Example 6 (Inhibition for Histamine Release)

Rat basophil leukemia cell line (RBL-2H3) suspended in a DMEM medium (manufactured by Invitrogen) supplemented with a 10% by volume fetal bovine serum (manufactured by Invitrogen) was seeded to a 96-well microtiter plate (manufactured by Corning) at a density of $1.4 \times 10^5$ cells/cm$^2$, and cultured at 37° C. under 5% $CO_2$ for 24 hours. Thereafter, the culture supernatant was removed by suction, a test solution as listed in Tables 6 to 8 was added thereto in a volume of 0.1 ml each per well, and the cultured cells were incubated at 37° C. for 1.5 hours under 5% $CO_2$ (Procedures 1). Here, as PIPES buffer, the following was used. PIPES buffer: pH 7.2, composition: 0.1 w/v % bovine serum albumin (manufactured by SIGMA), $CaCl_2.2H_2O$ 3.0 mM, $MgCl_2.6H_2O$ 0.40 mM, KCl 7.38 mM, NaCl 118.93 mM, D(+)-Glucose 5.60 mM, 25 mM PIPES (Piperazine-1,4-bis(2-ethanesulfonic acid), manufactured by DOJINDO LABORATORIES.

Thereafter, the culture supernatant was removed by suction, A23187 (reagent: manufactured by SIGMA) was further added to a test solution as listed in Tables 6 to 8 in a volume of 0.2 ml each per well, so as to have a concentration of 10 μM, and the cells were incubated at 37° C. for additional 30 minutes under 5% $CO_2$ (Procedures 2).

The supernatant of each well was collected, and the concentration of histamine was quantified using an ELISA kit (manufactured by Oxford Biochemical Research).

Also, as a control, a test was conducted in the same manner as the method mentioned above to quantify a histamine concentration, except that the PIPES buffer was used in place of a test solution in Procedures 1, and that PIPES buffer supplemented with A23187 was used in place of a test solution supplemented with A23187 in Procedures 2.

Further, as blank, a test was conducted in the same manner as the control to quantify a histamine concentration, except that PIPES buffer not supplemented with A23187 was used in Procedures 2.

Values resultant from subtracting the histamine concentration of the blank from the histamine concentrations of each test solution and the control are defined as a true histamine concentration of each test solution and a true histamine concentration of the control, respectively. Using the true histamine concentration of each test solution and the true histamine concentration of the control obtained, the rate of inhibiting histamine release (%) was calculated in accordance with the following formula (7).

$$\text{Rate of Inhibiting Histamine Release (\%)} = \left\{1 - \frac{\text{True Histamine Concentration of Each Test Solution}}{\text{True Histamine Concentration of Control}}\right\} \times 100 \quad (7)$$

Here, as the standards of the components used in the test, zinc chloride is a reagent manufactured by Wako Pure Chemical Industries, Ltd., and l-menthol is a reagent manufactured by Wako Pure Chemical Industries, Ltd.

TABLE 6

|  | Comp. Ex. 11 | Comp. Ex. 12 | Comp. Ex. 13 | Comp. Ex. 14 | Comp. Ex. 15 | Comp. Ex. 16 |
|---|---|---|---|---|---|---|
| Zinc Chloride | 0.0005 | — | — | — | — | — |
| Hypromellose | — | 0.2 | — | — | — | — |
| Carboxymethyl Cellulose Sodium | — | — | 0.2 | — | — | — |
| Polyethylene Glycol 4000 | — | — | — | 0.2 | — | — |
| Polyvinyl Pyrrolidone | — | — | — | — | 0.2 | — |
| Hydroxyethyl Cellulose | — | — | — | — | — | 0.2 |
| PIPES Buffer | q.s. | q.s. | q.s. | q.s. | q.s. | q.s. |
| pH | 7.3 | 7.3 | 7.3 | 7.3 | 7.3 | 7.3 |
| Rate of Inhibiting Histamine Release (%) | 4.0 | −6.4 | −2.0 | −5.5 | −10.7 | −5.5 |

Units of the content proportions of the components being w/v %.

TABLE 7

|  | Comp. Ex. 17 | Comp. Ex. 18 | Comp. Ex. 19 | Comp. Ex. 20 | Comp. Ex. 21 |
|---|---|---|---|---|---|
| l-Menthol | 0.01 | 0.01 | 0.01 | 0.01 | 0.01 |
| Hypromellose | 0.2 | — | — | — | — |
| Carboxymethyl Cellulose Sodium | — | 0.2 | — | — | — |
| Polyethylene Glycol 4000 | — | — | 0.2 | — | — |
| Polyvinyl Pyrrolidone | — | — | — | 0.2 | — |
| Hydroxyethyl Cellulose | — | — | — | — | 0.2 |
| PIPES Buffer | q.s. | q.s. | q.s. | q.s. | q.s. |
| pH | 7.3 | 7.3 | 7.3 | 7.3 | 7.3 |
| Rate of Inhibiting Histamine Release (%) | −10.3 | 0.7 | 4.9 | −4.3 | 0.4 |

Units of the content proportions of the components being w/v %.

TABLE 8

|  | Ex. 12 | Ex. 13 | Ex. 14 | Ex. 15 | Ex. 16 |
|---|---|---|---|---|---|
| Zinc Chloride | 0.0005 | 0.0005 | 0.0005 | 0.0005 | 0.0005 |
| l-Menthol | 0.01 | 0.01 | 0.01 | 0.01 | 0.01 |
| Hypromellose | 0.2 | — | — | — | — |
| Carboxymethyl Cellulose Sodium | — | 0.2 | — | — | — |
| Polyethylene Glycol 4000 | — | — | 0.2 | — | — |
| Polyvinyl Pyrrolidone | — | — | — | 0.2 | — |
| Hydroxyethyl Cellulose | — | — | — | — | 0.2 |
| PIPES Buffer | q.s. | q.s. | q.s. | q.s. | q.s. |
| pH | 7.3 | 7.3 | 7.3 | 7.3 | 7.3 |
| Rate of Inhibiting Histamine Release (%) | 30.3 | 27.0 | 33.2 | 23.5 | 28.5 |

Units of the content proportions of the components being w/v %.

As is clear from Tables 6 to 8, Comparative Example 11 in which a test solution containing only zinc chloride was used slightly showed an inhibitory action for histamine release, but Comparative Examples 12 to 16 in which a test solution containing a component (C) alone was used showed the tendencies of rather decreasing an inhibitory effect for histamine release. In addition, Comparative Examples 17 to 21 in which a test solution containing menthol in addition to the component (C) also were hardly found to have any improvements in the inhibitory effect for histamine release.

By contrast, Examples 12 to 16 in which a test solution containing zinc chloride, a component (C), and menthol was used had marked improvements in the effect of inhibiting histamine release, thereby exhibiting a large effect of inhibiting histamine release.

Test Example 7 (Inhibitory Test for Discharges from the Eyes)

Test solutions were prepared in accordance with a formulation as listed in Table 9, and filled in an eye drop container made of PET to give a test sample. A tested individual was instilled into the eyes two kinds of test samples as one set, one set of the test sample instilling into the right eye, and the other set instilling into the left eye, one set per day, five times a day, 2 drops each time (n=10). Here, one kind of the test sample was always instilled into the identical eye, and the intervals of instillations between each time were kept one or more hours. After 2 hours or more from the fifth instillation into the eyes, the amount of discharges from the eyes which the tested individual subjectively sensed was evaluated in accordance with a visual analogue scale method (VAS method). In other words, on a straight line of 10 cm in length, the left end of the straight line, i.e. a point at 0 cm is defined as "no discharges from the eyes being found," and the right end of the straight line, i.e. a point at 10 cm is defined as "maximum amount of discharges from the eyes which was experienced in the past being found," the tested individual was asked to show one point on the straight line that corresponds to the amount of discharges from the eyes which is subjectively sensed in the eyes after the instillation into the eyes of each of test samples, the distance (cm) from the point at 0 cm was measured and defined as scores on the amount of discharges from the eyes. The results are also shown together in Table 9. The units of the content proportions of the components in Table 9 are w/v %.

TABLE 9

| | Name of Set | | | |
|---|---|---|---|---|
| | Set A | | Set B | |
| | Right Eye/Left Eye | | | |
| Test Solution Name | Right Eye Comp. Ex. 22 | Left Eye Comp. Ex. 23 | Right Eye Comp. Ex. 24 | Left Eye Ex. 17 |
| Zinc Chloride | — | 0.002 | — | 0.002 |
| l-Menthol | — | — | 0.01 | 0.01 |
| Polysorbate 80 | 0.04 | 0.04 | 0.04 | 0.04 |

TABLE 9-continued

| | Name of Set | | | |
|---|---|---|---|---|
| | Set A | | Set B | |
| | Right Eye/Left Eye | | | |
| Test Solution Name | Right Eye Comp. Ex. 22 | Left Eye Comp. Ex. 23 | Right Eye Comp. Ex. 24 | Left Eye Ex. 17 |
| Hydroxyethyl Cellulose | — | — | 0.01 | 0.01 |
| Boric Acid | 1 | 1 | 1 | 1 |
| Sodium Chloride | 0.4 | 0.4 | 0.4 | 0.4 |
| Borax | q.s. | q.s. | q.s. | q.s. |
| Purified Water | q.s. | q.s. | q.s. | q.s. |
| pH | 7.2 | 7.2 | 7.2 | 7.2 |
| Amount of Discharges from the Eyes (Average) | 6.4 | 5.8 | 6.7 | 2.5 |

As is clear from Table 9, the test solution of Example 17 containing zinc chloride and menthol, and further containing hydroxyethyl cellulose as a component (C) was found to have a remarkable inhibitory effect on the amount of discharges from the eyes.

The invention claimed is:

1. A method for inhibiting adsorption of a terpenoid in an aqueous ophthalmic composition to a container, comprising:
   combining in the aqueous ophthalmic composition (B) zinc chloride and (C) at least one member selected from the group consisting of cellulose-based polymeric compounds, vinyl-based polymeric compounds, polyethylene glycols and dextran, together with (A) a terpenoid.

2. A method for enhancing an inhibitory action for histamine release of an aqueous ophthalmic composition, comprising:
   combining in the aqueous ophthalmic composition (A) a terpenoid, (B) zinc chloride, and (C) at least one member selected from the group consisting of cellulose-based polymeric compounds, vinyl-based polymeric compounds, polyethylene glycols and dextran.

3. A method for giving an inhibitory action for discharges from the eyes to an aqueous ophthalmic composition, comprising:
   combining in the aqueous ophthalmic composition (A) a terpenoid, (B) zinc chloride, and (C) at least one member selected from the group consisting of cellulose-based polymeric compounds, vinyl-based polymeric compounds, polyethylene glycols and dextran.

* * * * *